(12) United States Patent
Laxhuber et al.

(10) Patent No.: US 9,095,401 B2
(45) Date of Patent: Aug. 4, 2015

(54) SUPPORT SYSTEM AND METHOD FOR VIEWER-DEPENDENT POSITIONING AND ALIGNMENT OF A DISPLAY UNIT

(75) Inventors: Ludwig Laxhuber, Herrsching (DE); Stefan Kaltenbach, Rebstein (CH); Joachim Luber, St. Margrethen (CH)

(73) Assignee: Forstgarten International Holding GmbH, St. Gallen (CH)

( * ) Notice: Subject to any disclaimer, the term of this patent is extended or adjusted under 35 U.S.C. 154(b) by 1734 days.

(21) Appl. No.: 12/517,983

(22) PCT Filed: Dec. 4, 2007

(86) PCT No.: PCT/EP2007/010526
§ 371 (c)(1),
(2), (4) Date: Mar. 11, 2011

(87) PCT Pub. No.: WO2008/067994
PCT Pub. Date: Jun. 12, 2008

(65) Prior Publication Data
US 2012/0013723 A1 Jan. 19, 2012

Related U.S. Application Data

(60) Provisional application No. 60/868,958, filed on Dec. 7, 2006.

(30) Foreign Application Priority Data

Dec. 7, 2006 (EP) .................................. 06025363

(51) Int. Cl.
*H04N 9/47* (2006.01)
*H04N 7/18* (2006.01)
(Continued)

(52) U.S. Cl.
CPC ............... *A61C 19/00* (2013.01); *F16M 11/04* (2013.01); *F16M 11/08* (2013.01); *F16M 11/18* (2013.01);
(Continued)

(58) Field of Classification Search
CPC ......... H04N 5/64; H04N 5/645; H04N 5/655; G06F 1/1637; G06F 1/1641
USPC ................... 348/77, 787, 788, 789, 794, 836
See application file for complete search history.

(56) References Cited

U.S. PATENT DOCUMENTS 5,732,712 A * 3/1998 Adair ............................ 128/845
7,443,417 B1 * 10/2008 Heinrich ......................... 348/66
(Continued)

FOREIGN PATENT DOCUMENTS

DE    19719038 A1    11/1998
FR    2606915 A1    5/1988
(Continued)

*Primary Examiner* — Jeremaiah C Hallenbeck-Huber
(74) *Attorney, Agent, or Firm* — McDonnell Boehnen Hulbert & Berghoff LLP

(57) ABSTRACT

A support system (10) and method for the viewer-dependent positioning and alignment of a monitor (20) is disclosed. The support system (10) comprises a central support column (14), a first arm (16) having an adjustable length L, wherein the first arm (16) is rotatably connected at its proximal end to the central support column (14) and is pivotally connected at its distal end to the monitor (20), a second arm (18), wherein the second arm (18) is connected at its distal end to a camera (50), and control means for positioning and aligning the monitor (20) such that irrespective of the angular position of the viewer (i) the monitor (20) is positioned along the line of sight of the viewer pointing towards a reference position, (ii) the distance from the monitor (20) to the viewer (40) is held constant, and (iii) the monitor (20) is at a right angle with respect to the line of sight of the viewer (40) pointing towards a reference position.

15 Claims, 3 Drawing Sheets

(51) Int. Cl.
- *A61C 19/00* (2006.01)
- *F16M 11/04* (2006.01)
- *F16M 11/08* (2006.01)
- *F16M 11/18* (2006.01)
- *F16M 11/20* (2006.01)
- *G06F 1/16* (2006.01)
- *H04N 5/645* (2006.01)
- *H04N 5/655* (2006.01)

(52) U.S. Cl.
CPC ..... *F16M 11/2014* (2013.01); *F16M 2200/068* (2013.01); *G06F 1/1637* (2013.01); *G06F 1/1641* (2013.01); *H04N 5/645* (2013.01); *H04N 5/655* (2013.01)

(56) References Cited

U.S. PATENT DOCUMENTS

| | | | |
|---|---|---|---|
| 2003/0021107 A1* | 1/2003 | Howell et al. | 362/147 |
| 2003/0058372 A1* | 3/2003 | Williams et al. | 348/836 |
| 2004/0073931 A1* | 4/2004 | Trussell et al. | 725/74 |
| 2004/0201595 A1* | 10/2004 | Manchester | 345/649 |
| 2004/0246469 A1 | 12/2004 | Hirose | |
| 2006/0071135 A1* | 4/2006 | Trovato | 248/289.11 |
| 2006/0244749 A1 | 11/2006 | Kondo et al. | |
| 2006/0250684 A1* | 11/2006 | Sander | 359/368 |
| 2006/0252004 A1* | 11/2006 | Donahoo | 433/29 |
| 2007/0276250 A1* | 11/2007 | Donaldson | 600/459 |

FOREIGN PATENT DOCUMENTS

| | | |
|---|---|---|
| JP | 06-309067 | 11/1994 |
| JP | 06309067 | 11/1994 |
| JP | 2003186411 | 7/2003 |
| JP | 2003186411 A | 7/2003 |
| JP | 2006311343 | 11/2006 |
| WO | 2004/052225 A2 | 6/2004 |
| WO | 2006/119445 A2 | 11/2006 |

* cited by examiner

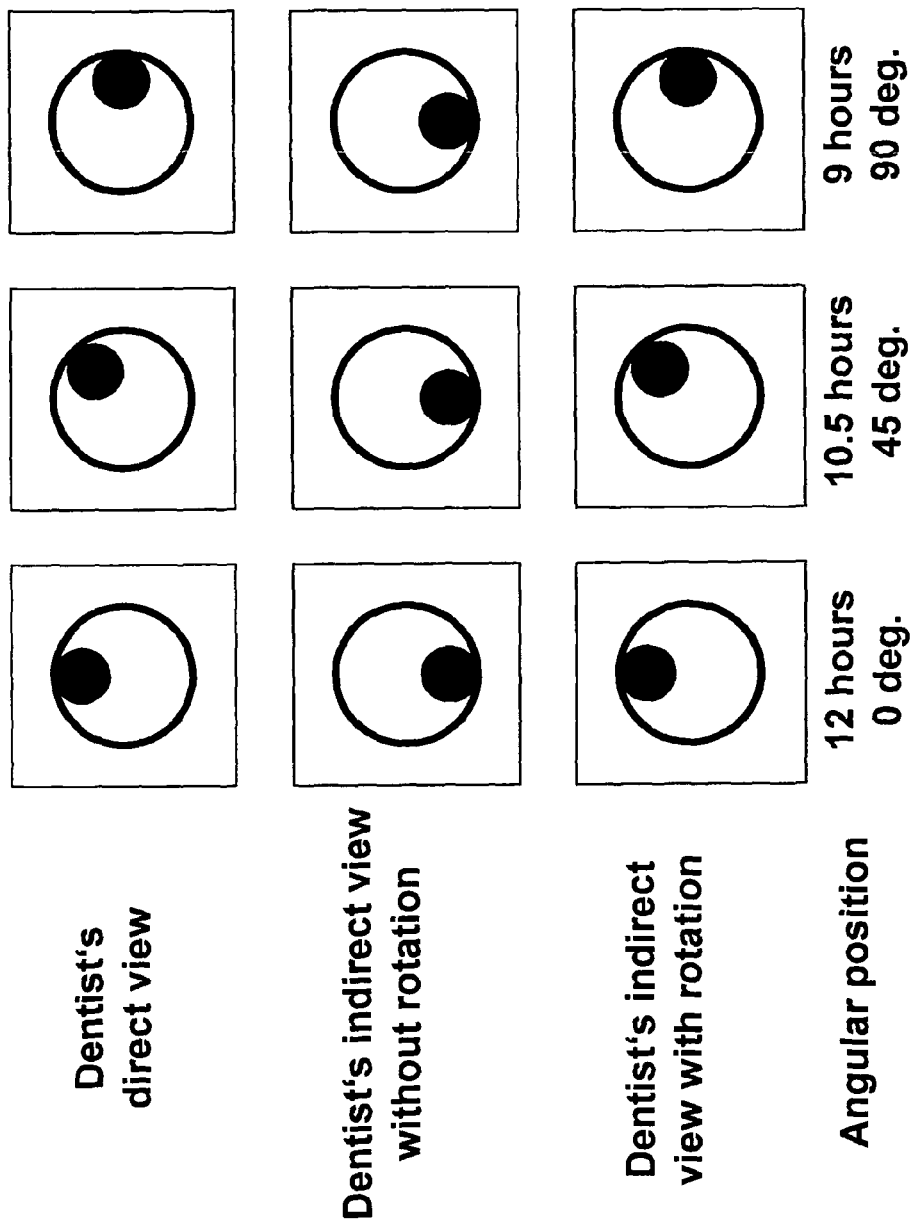

SUPPORT SYSTEM AND METHOD FOR VIEWER-DEPENDENT POSITIONING AND ALIGNMENT OF A DISPLAY UNIT

TECHNICAL FIELD OF THE INVENTION

The invention relates to a support system and method for automatically positioning and aligning a display unit, preferably a monitor, depending on the position of a viewer. In particular, the invention relates to such a system and method which beneficially can be employed by a dentist.

BACKGROUND OF THE INVENTION

Besides the usual visual inspection dentists or dental surgeons more and more employ imaging devices, such as cameras and monitors, in order to assist them in examining and providing an appropriate treatment of the dental region of a patient. That is, often the dental region of a patient who usually is sitting on a dentist's chair is visually examined directly by the dentist who is sitting at either side of the patient and "indirectly" by a camera which often is located at some position above the patient and aimed at the dental region of the patient. The image acquired by the camera is displayed on a monitor that is appropriately positioned such that it can be looked at by the dentist. However, conventionally the position of the monitor is stationary or has to be adjusted manually by the dentist. In other words, without a manual adjustment only in a certain position the dentist will have a full face-on view of the monitor. In other positions angularly offset from this optimum position the dentist will be looking under an angle at the monitor. However, even if the position of the monitor can be manually adjusted such a task interferes with the work of the dentist and, thus, restricts his ability to freely move around and to ensure an appropriate treatment.

The object of the present invention is to provide such a system overcoming or at least mitigating the problems associated with conventional systems.

SUMMARY OF THE INVENTION

This object is achieved by a support system according to claim 1 of the present invention.

In the context of the working environment of a dentist it is possible by means of the support system according to the present invention to automatically adjust and align the position of a monitor mounted to the support system such that irrespective of the position of the dentist (i) the monitor is positioned along the line of sight of the dentist pointing in the direction of the dental region of a patient, (ii) the distance from the monitor to the dentist is constant, and (iii) the monitor is at a right angle with respect to the line of sight of the dentist pointing in the direction of the dental region of the patient.

Further preferred beneficial embodiments are defined in the sub-claims.

BRIEF DESCRIPTION OF THE DRAWINGS

FIG. 2 shows schematically the correspondence between the dentist's direct view of an object of interest and the image being displayed on the monitor of the support system according to the present invention.

DETAILED DESCRIPTION OF PREFERRED EMBODIMENTS

Figure 1:
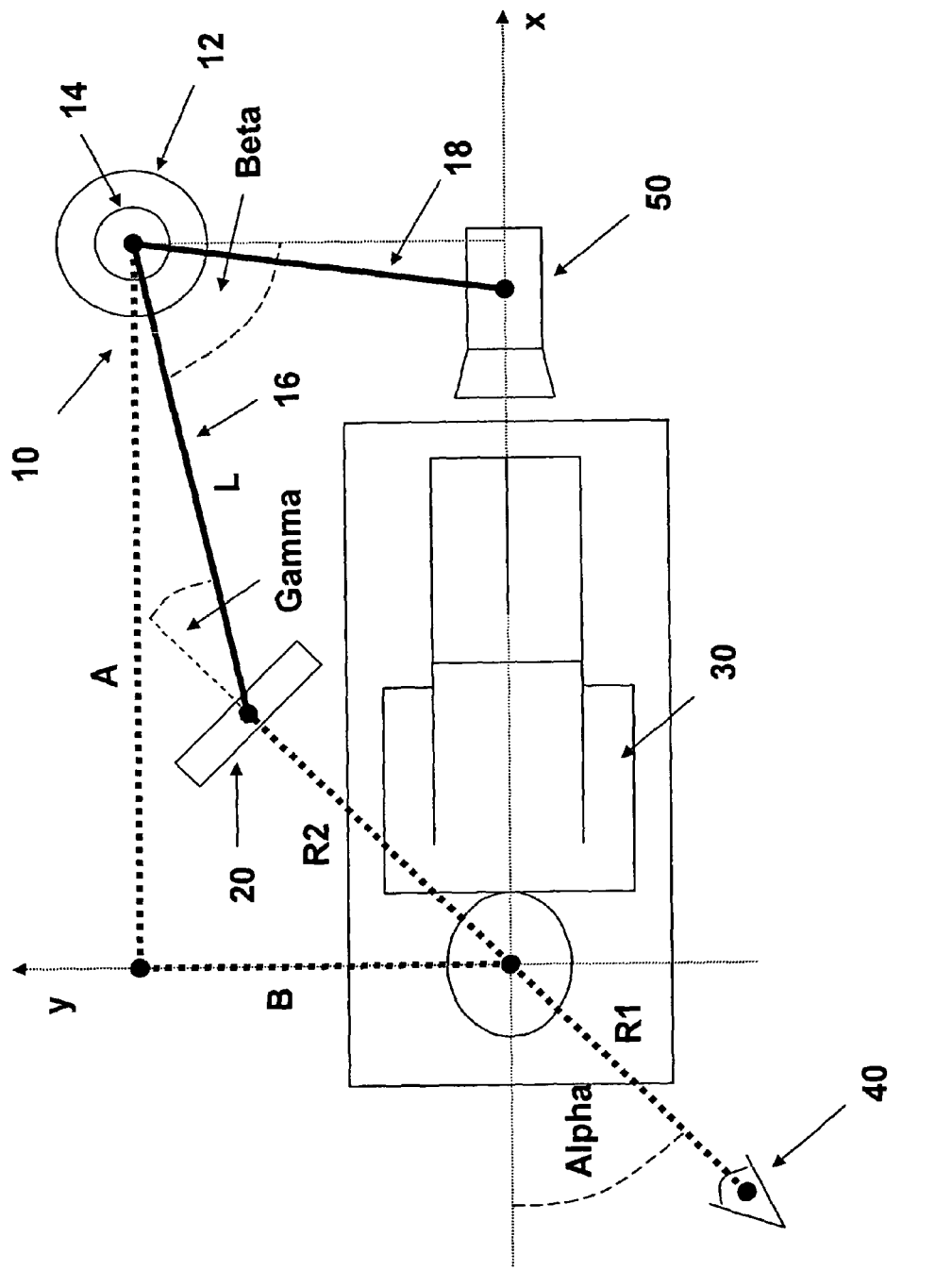
FIG. 1 shows schematically a plan view of the support system according to a preferred embodiment of the present invention.

A first preferred embodiment of the support system 10 according to the present invention is shown in FIG. 1. As shown, the support system 10 comprises a base 12 and a central support column 14 extending upwardly from the base 12 which in turn can be fixedly mounted to the floor. Alternatively, the central support column 14 of the support system 10 equally could be fixedly mounted to a wall or a ceiling, such that no base 12 would be required. Furthermore, the central support column 14 of the support system 10 also could be resting on a movable base such that the support system 10 according to the present invention can be moved to a desired location.

A first arm 16 of the support system 10 is rotationally connected with its proximal end to the central support column 14 and extends away therefrom. The first arm 16 is pivotally connected at its other, i.e. distal, end to a monitor 20. The monitor 20 is affixed to the distal end of the first arm 16 such that the monitor 20 can be pivoted in such a way that the angle between the first arm 16 and the normal of the monitor 20 can be varied. Furthermore, as will be discussed in more detail further below, the length L of the first arm 16 can be adjusted by appropriate control means (not shown) being part of and preferably integrated into the support system 10.

Preferably, the support system 10 further includes a second arm 18 also extending away from the central support column 14 of the support system 10. At the end of the second arm 18 distal to the central support column 14 of the support system 10 a camera 50 is mounted. Preferably, also the length of the second arm 18 can be adjusted by the control means. As the person skilled in the art will appreciate, the first arm 16 and the second arm 18 should be connected to the central support column 14 of the support system 10 such that these two arms can be rotated freely about the central support column 14 of the support system 10 without interfering with each other. For instance, this can be readily achieved by connecting the first arm 16 and the second arm 18 to the central support column 14 of the support system 10 at different heights thereof. Preferably, the first arm 16 and the second arm 18 are adjustable in height. The camera 50 mounted to the distal end of the second arm 18 points at a region to be imaged, preferably the dental region of a patient 30, and the acquired image is displayed on the monitor 20. The person skilled in the art will further appreciate that an appropriate support system 10 and the components thereof can be made out of a variety of elements, such as support rods or telescope arms, hinged connections connecting these elements and the like. Therefore, the details of these elements will not be described in any greater detail herein.

Referring to FIG. 1 again, a patient 30 is sitting/lying on a dentist's chair and defines for illustrative purposes a two dimensional horizontal coordinate system with the origin, i.e. the reference position, coinciding with the dental region of the patient 30 and the x-axis coinciding with the symmetry axis of the dentist's chair. The y-axis lies perpendicular to the x-axis in a horizontal plane. With respect to a such defined coordinate system the center of the base 12 and in turn the central support column 14 of the support system 10 according to the present invention are located at the coordinates x=A and y=B. The dentist 40 is located at a horizontal distance R1 from the origin to the right of the patient such that the line of sight of the dentist in the direction of the region of interest, i.e. the dental region of the patient 30, defines an angle α (Alpha) with the x-axis as shown in FIG. 1, hereinafter also referred to as the "angular position" of the dentist 40. According to the present invention the extension of this line of sight will "strike" after an additional horizontal distance R2 the monitor 20 located in a non delimiting manner to the left of the patient 30. Due to the support system 10 according to the present invention the dentist 40 irrespective of his position always will have a full face-on view of the monitor 20 at a constant horizontal distance R1+R2. According to the present invention this is achieved by an appropriate automatic adjustment and positioning of the position of the monitor 20 as a function of the position of the dentist 40. As mentioned above, the support system 10 according to the present invention comprises control means arranged and configured to automatically adjust and position the monitor 20 in a way as described below.

According to the present invention the length L of the first arm 16 of the support system 10 connecting the monitor 20 with the central support column 14 can be adjusted by the control means of the support system 10 as a function of the angular position a of the dentist 40 as follows:

$$L(\alpha)=((A-R2^*\cos(\alpha))^2+(B-R2^*\sin(\alpha))^2)^{1/2} \quad \text{(Eq. 1)}$$

As can be taken from this formula for fixed A, B (i.e. a fixed position of the base 12 and the central support column 14 of the support system 10 relative to the patient 30) and R2, the length L of the first arm 16 depends only on the angular position a of the dentist 40.

However, in case the position of the dentist changes not only the length L of the first arm 16 but also two additional quantities have to be adjusted, namely the angle β (Beta) defined by the first arm 16 of the support system 10 and the parallel to the y-axis running through the center of the base 12 and the angle γ (Gamma) defined by the first arm 16 of the support system 10 and the normal to the surface of the monitor 20, as shown in FIG. 1. The position of the dentist 40 could also change at a given angular position a by moving closer to or further away from the patient 30 such that R1 decreases or increases. Although according to the preferred embodiment such a change of the position of the dentist 40 at a fixed angular position a does not have an effect on the positioning and the alignment of the monitor 20, the person skilled in the art will appreciate that the support system according to the present invention and the control means thereof also can be configured to adjust the position and the alignment of the monitor 20 such that the distance from the dentist 40 to the monitor 20, i.e. R1+R2, remains constant.

According to the present invention the angle β between the first arm 16 and the parallel to the y-axis running through the center of the base 12 is adjusted by the control means of the support system 10 as a function of the angular position a of the dentist 40 as follows:

$$\beta = \cos^{-1}\left(\frac{L(\alpha)^2 + B^2 - (R2^2 + A^2 - 2*R2*A*\cos(\alpha))}{2*L(\alpha)*B}\right) \quad \text{(Eq. 2)}$$

The adjustment of the angle γ between the first arm 16 and the normal to the surface of the monitor 20 is effected by the control means of the support system 10 according to the following formula:

$$\gamma = 180° - \cos^{-1}\left(\frac{R2 + L(\alpha)^2 - (A^2 + B^2)}{2*R2*L(\alpha)}\right) \quad \text{(Eq. 3)}$$

As the person skilled in the art will appreciate, the adjustment of the length L of the first arm 16 and the angles β and γ, as outlined above, by the control means of the support system 10 according to the present invention ensures that irrespective of the position of the dentist 40 (i) the monitor 20 is positioned along the line of sight of the dentist 40 pointing in the direction of the dental region of the patient 30, (ii) the distance R1+R2 from the monitor 20 to the dentist 40 is constant, and (iii) the monitor 20 is at a right angle with respect to the line of sight of the dentist 40 pointing in the direction of the dental region of the patient 30.

Instead of a "mechanical" adjustment of the length L of the first arm 16 depending on the position of the viewer 40, L also could be held constant and the control means of the support system 10 according to the present invention could be configured to adjust the size of the image in such a way that irrespective of the position of the viewer 40 the ratio of the size of the image displayed on the monitor 20 to the distance of the viewer 40 to the monitor 20 is held constant. In other words, if the distance of the viewer 40 to the monitor 20 is decreasing then also the size of the image displayed on the monitor 20 should be decreasing and vice versa. To this end an appropriately configured software algorithm could be implemented in the control means for adjusting the image size in relation to the position of the viewer 40 such that irrespective of the position of the viewer 40 features within the image will always appear with the same size. The person skilled in the art will appreciate that even in case the length L of the first arm 16 is held constant the above equations 2 and 3 still can be used in order to compute the position and the alignment of the monitor 20, i.e. the angles β and γ, in relation to the position of the viewer 40.

Although FIG. 1 shows only a single monitor. 20 and a single camera 50, the support system 10 according to the present invention is able to support more than one display unit and more than one imaging unit. For instance, the support system 10 according to the present invention could be configured to support a conventional monitor and a stereoscopic monitor as well as a conventional camera or microscope and a stereo camera or microscope. These units could each be supported by a respective arm of the support system 10 according to the present invention. Alternatively, the support system 10 according to the present invention could support by means of a single arm a display unit being configured as a conventional monitor on one side and as a stereoscopic monitor on the other side. In such a case, the dentist simply would have to rotate the display unit by 180° in order to change between the conventional monitor and the stereoscopic monitor and vice versa.

The first arm 16 as shown in FIG. 1 is configured as a single telescope arm which can be rotated angularly around the central support column 14 of the support system 10 and the length L thereof can be adjusted by extension or retraction. The person skilled in the art, however, will appreciate that the first arm 16 equally could be provided by two hingedly connected rods of fixed length. Furthermore, the person skilled in the art will appreciate that appropriate stabilizing means may be necessary to stabilize the support system 10 according to the present invention by means of counter weights, fluid tanks or the like.

Preferably, the position of the dentist 40 is monitored by position detection means or a position detector (not shown) well known in the art. Such position detection means provide the control means of the support system 10 according to the present invention with the necessary information, i.e. the dentist's angular position α, in order to determine the length L of the first arm 16, the angle β and the angle γ, as outlined above, and to adjust and position the monitor 20 accordingly. Thus, preferably, the adjustment and the positioning of the monitor 20 of the support system 10 according to the present invention are performed fully automatically by the control means. Preferably, the determination of the position of the dentist 40 and the subsequent adjustment of the position of the monitor 20 by the control means of the support system 10 is performed at certain intervals, such as every second.

In an alternative embodiment without position detection means the control means of the support system 10 can be provided with the angular position of the dentist by means of information provided by the dentist 40 himself. For instance, the dentist 40 could issue a voice command, such as "10 o'clock" (corresponding to an angle α of 60°), which would cause the control means of the support system 10 to adjust the length L of the first arm 16 and the angles β and γ, as outlined above (Equations 1 to 3), accordingly. The person skilled in the art will appreciate that instead of voice commands the dentist 40 could also provide information about his angular position by means of a key pad, a turning knob or the like connected to the control means of the support system 10 according to the present invention. In order to assist the dentist in determining his angular position himself and providing the same to the control means, it is envisaged e.g. that appropriate elongate markings are provided on the floor supporting the dentist chair, such as lines marked "12 o'clock", "11 o'clock", "10 o'clock", "9 o'clock" and so on corresponding to angular positions a of 0°, 30°, 60° and 90° (a structure also known as the "Kaltenbach Circle").

By means of the above-described positioning and alignment of the monitor 20 according to the present invention it is possible, as already mentioned above, to ensure that (i) the monitor 20 is positioned along the line of sight of the dentist 40 pointing in the direction of the dental region of the patient 30, (ii) the distance from the monitor 20 to the dentist 40 is constant, and (iii) the monitor 20 is disposed at a right angle with respect to the line of sight of the dentist 40 pointing in the direction of the dental region of the patient 30. Once the positioning and alignment of the monitor 20 have been achieved by the control means of the support system 10 according to the present invention, said control means according to a further preferred aspect of the present invention allow for the adjustment of the angular orientation of the image displayed on the monitor.

This further aspect of the present invention is based on the following idea: if the camera 50 is positioned along the symmetry or longitudinal axis of the dentist's chair, as is often the case and shown in FIG. 1, the camera 50 normally will image a certain portion of the dental region of the patient 30 and display that image on the monitor 20 in such a way that the upper portion of the dental region of the patient is displayed on the upper portion of the monitor 20, i.e. in an "upright orientation". Now, if the dentist is positioned at an angular position of e.g. α equal to 90°, then the monitor 20 will be positioned in FIG. 1 along the y-axis at a distance R2 from the dental region of the patient 30 and at a distance R1+R2 from the dentist 40. If in this configuration the dentist 40 looks "directly" at the dental region of the patient he will perceive the same in such a way that the upper portion of the dental region of the patient is on the left side of his field of view and the lower portion is to the right thereof, i.e. not in an "upright" orientation but in a "horizontal" orientation. Furthermore, a motion e.g. of the dentist's hand equipped with a dental instrument occurring within the field of view of the camera e.g. in the direction of the positive y-axis will be displayed on the monitor as a corresponding motion from left to right. As the person skilled in the art will appreciate, this different orientations of the "direct" view and the "indirect" view via the camera 50 and the monitor 20 of the dental region of the patient 30 might be confusing to the dentist 40 and detrimental to the success of any treatments, in particular when the dentist has to switch between these two views during a treatment.

Therefore, the control means of the support system 10 are preferably further adapted to adjust the angular orientation of the image to be displayed on the monitor 20 in such a way that the view displayed on the monitor 20 corresponds to the dentist's direct view of the dental region of the patient 30. According to a preferred embodiment this is achieved by means of an appropriately configured software algorithm implemented in the control means of the support system 10 according to the present invention. The images acquired by the camera 50 and transferred to the control means will be processed by means of this software algorithm in accordance with the angular position a of the dentist 40 and the processed image will be displayed on the monitor 20. As the person skilled in the art will appreciate the software algorithm essentially could be provided by an image rotation algorithm with the rotation angle being given by 180°-α. In an alternative embodiment, the adjustment of the angular orientation of the image to be displayed is achieved by a mechanical rotation of the camera 50 about its longitudinal axis by means of the control means of the support system according to the present invention.

FIG. 2 illustrates schematically the relationship between the "direct" view of the dentist 40 (images in upper line), the image acquired without rotation of the camera 50 (images in middle line) and the image acquired with an rotation of the camera 50 or provided by the image rotation software algorithm implemented in the control means according to the present invention (images in lower line) for three different angular positions of the dentist 40, namely α=0°, 45° and 90°. The images shown in the lower line of FIG. 2 also illustrate in rather schematically what according to the present invention is actually displayed on the monitor 20 and correspond to the "direct" views of the dentist shown in the upper line of FIG. 2.

A further aspect of the invention provides for an automatic "lock-in" mechanism of the camera 50 onto the dental region of the patient 30 to be imaged. To this end, the dental region of the patient 30 is provided with locations means, such as two markers disposed at the right and the left end of the mouth of the patient 30. The control means of the support system 10 are configured to locate these markers in the image provided by the camera 50 and will provide the camera 50 with a corresponding feedback to adjust the distance and/or the focus such that the two markers are located at the right end and the left end of the field of view of the camera 50.

Figure 3C:
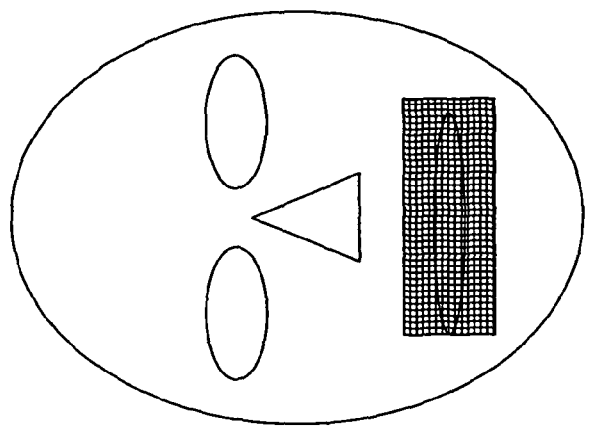
FIGS. 3a, 3b, and 3c show schematically a further aspect of the present invention.
Figure 3B:
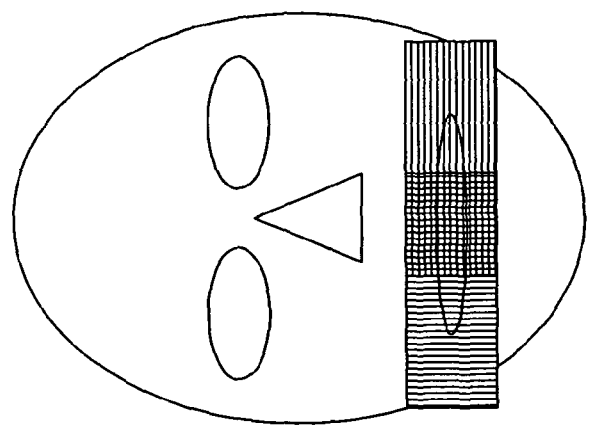
Figure 3A:
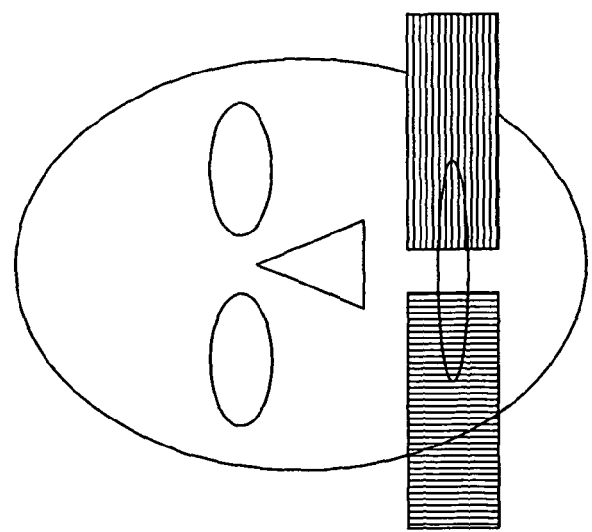

In order to reduce the number of manual adjustments of the second arm 18 of the support system 10 and in turn the camera 50 connected to the distal end thereof as much as possible, a further aspect of the present invention provides for the automatic adjustment, and in particular focusing, of the camera 50 by means of a two dimensional positioning beam. As schematically shown in FIGS. 3a, 3b and 3c, the camera 50 projects two two-dimensional, e.g. rectangular, light beams or positioning beams onto the region to be imaged, i.e. the dental region of the patient 30. A single two-dimensional positioning beam would be sufficient in order to indicate the current field of view of the camera by means of an appropriate illumination of the region to be imaged. However, preferably, a second two-dimensional positioning beam is projected onto the region to be imaged. As schematically indicated by means of the different hatching angles, the two two-dimensional positioning beams preferably have different colors, such as additive colors, yellow and blue or the like. The region where the two two-dimensional positioning beams overlap will appear in a different color, such as green. The distance of the camera 50 to the region to be imaged and/or the internal optics of the camera 50 are adjusted manually or automatically as long as the two two-dimensional positioning beams do not fully overlap, i.e. as long as different colors are present. Once only one color is present, i.e. the two beams completely overlap, as shown in FIG. 3c, the camera 50 is in focus. In this case, the area illuminated by the two positioning beams corresponds to the field of view of the camera 50 being in focus. Preferably, the camera 50 allows for an adjustment of the internal lighting thereof to adjust the same such that only the field of view of the camera 50 gets illuminated.

The present invention as described in detail above is not limited to the particular devices, uses and methodology described as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

The person skilled in the art will appreciate, in particular, that the spatial orientations illustrated in the figures, i.e. the dentist being located to the right and the support system being essentially located to the left to the patient, have been chosen for illustrative purposes only and should in no way be construed as to limit the scope of protection as defined by the appended claims.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

The invention claimed is:

1. Support system for the viewer-dependent positioning and alignment of a monitor, comprising:
a central support column;
a first arm having an adjustable length L, wherein the first arm is rotatably connected at its proximal end to the central support column and is pivotally connected at its distal end to the monitor;
a second arm, wherein the second arm is connected at its distal end to a camera providing image data to the monitor of an object of interest defining a reference position; and
control means for positioning and aligning the monitor such that irrespective of the position of the viewer the monitor is positioned along the line of sight of the viewer pointing towards the reference position, the distance from the monitor to the viewer is held constant, and the monitor is at a right angle with respect to the line of sight of the viewer pointing towards the reference position, wherein the control means are configured to adjust the length L of the first arm as a function of the angular position α of the viewer as follows:

$$L(\alpha) = ((A - R2*\cos(\alpha))^2 + (B - R2*\sin(\alpha))^2)^{1/2},$$

wherein R2 is the horizontal distance from the reference position to the monitor, A is the horizontal distance from the reference position to the central support column projected onto a x-axis and B is the horizontal distance from the reference position to the central support column projected onto a y-axis,
wherein the x-axis is defined by the horizontal line connecting the reference position and the camera and the y-axis is disposed horizontally in a perpendicular relationship with the x-axis.

2. Support system according to claim 1, wherein the control means are configured to adjust an angle β defined between the first arm and the parallel to the y-axis running through the center of the central support column as a function of the angular position α of the viewer as follows:

$$\beta = \cos^{-1}\left(\frac{L(\alpha)^2 + B^2 - (R2^2 + A^2 - 2*R2*A*\cos(\alpha))}{2*L(\alpha)*B}\right).$$

3. Support system according to claim 1, wherein the control means are configured to adjust an angle γ defined between the first arm and a normal to the surface of the monitor as a function of the angular position α of the viewer as follows:

$$\gamma = 180° - \cos^{-1}\left(\frac{R2 + L(\alpha)^2 - (A^2 + B^2)}{2*R2*L(\alpha)}\right).$$

4. Support system according to claim 1, wherein the central support column is fixedly attached to a base or configured to be fixedly attached to a wall or a ceiling.

5. Support system according to claim 1, wherein the first arm is a telescope arm.

6. Support system according to claim 1, wherein the first arm comprises two hingedly connected rods of fixed length.

7. Support system according to claim 1, further comprising stabilizing means.

8. Support system according to claim 1, wherein the angular position of the viewer can be input by means of voice command, a key pad and/or a turning knob and transmitted to the control means.

9. Support system according to claim 1, further comprising means for adjusting the angular orientation of the image displayed by the monitor in dependence of the angular position of the viewer.

10. Support system according to claim 9, wherein the angular orientation of the image displayed by the monitor is adjusted by means of an image rotation performed by the control means.

11. Support system according to claim 9, wherein the angular orientation of the image displayed by the monitor is adjusted by means of a rotation performed by the camera.

12. Support system according to claim 1, wherein the control means are configured to adjust the camera such that the field of view of the camera corresponds to the dental region of the patient.

13. Support system according to claim 1, wherein the camera projects two two-dimensional positioning beams corresponding to the field of view thereof onto the region to be imaged having different additive colors and the camera is in focus, if the two two-dimensional positioning beams overlap completely.

14. Support system according to claim 9, wherein the camera comprises internal lighting means arranged and configured to illuminate only the field of view thereof.

15. Method for operating a support system according to claim 1, comprising the step of positioning and aligning the monitor in response to the position of the viewer.

\* \* \* \* \*